(12) United States Patent
Bort

(10) Patent No.: US 8,118,762 B2
(45) Date of Patent: Feb. 21, 2012

(54) MEDICAL KNEE BANDAGE

(75) Inventor: Rudi Bort, Weinstadt (DE)

(73) Assignee: Bort GmbH, Weinstadt (DE)

( * ) Notice: Subject to any disclaimer, the term of this patent is extended or adjusted under 35 U.S.C. 154(b) by 135 days.

(21) Appl. No.: 11/171,264

(22) Filed: Jul. 1, 2005

(65) Prior Publication Data

US 2006/0004315 A1    Jan. 5, 2006

(30) Foreign Application Priority Data

Jul. 2, 2004  (DE) .................... 20 2004 010 779 U

(51) Int. Cl.
*A61F 5/00* (2006.01)
*A61F 13/00* (2006.01)

(52) U.S. Cl. ................. 602/23; 602/26; 602/60; 602/61

(58) Field of Classification Search .................... 24/381, 24/387, 390, 432; 602/60–65, 20, 23, 26; D24/190–192; 2/455, 16, 22, 24
See application file for complete search history.

(56) References Cited

U.S. PATENT DOCUMENTS

| 1,258,052 A * | 3/1918 | Stall ................................ 602/63 |
| 1,708,144 A * | 4/1929 | Martin ............................. 36/2 R |
| 1,775,714 A | 12/1929 | Bass |
| 2,012,755 A | 7/1934 | DeMuth |
| 2,280,025 A | 8/1940 | Bollinger |
| 2,246,100 A * | 6/1941 | Marzani ............................ 54/82 |
| 2,431,287 A * | 11/1947 | Washington ....................... 2/239 |
| 3,193,984 A * | 7/1965 | Schubert ........................... 54/82 |
| 4,870,956 A * | 10/1989 | Fatool et al. .................... 602/26 |
| 5,010,597 A * | 4/1991 | Glover .............................. 2/242 |
| 5,139,477 A * | 8/1992 | Peters ............................. 602/26 |
| 5,653,244 A | 8/1997 | Shaw |

FOREIGN PATENT DOCUMENTS

DE     202 07 156    9/2002
GB     2077565       12/1981

OTHER PUBLICATIONS

European Search Report dated Nov. 6, 2008.

* cited by examiner

*Primary Examiner* — Kim M Lewis

(74) *Attorney, Agent, or Firm* — Crowell & Moring LLP

(57) ABSTRACT

A medical knee bandage having a sheathing body of material that is elastic in at least some sections and is open on opposing ends and forms a closed sheathing jacket that is under tangential elastic stress when applied around a human knee area. A removal aid which is designed as a separation that is closable, for example by a zipper, extends over some or all of the length of the sheathing body.

8 Claims, 4 Drawing Sheets

MEDICAL KNEE BANDAGE

This application claims the priority of German Application No. 20 2004 010 779.1, filed Jul. 2, 2004, the disclosure of which is expressly incorporated by reference herein.

BACKGROUND AND SUMMARY OF THE INVENTION

The invention relates to a medical knee bandage having a sheathing body made of a material that is elastic in at least some sections and is open on the opposing ends and, when applied in the functional state, forms a closed sheathing material stretched elastically tangentially around a human knee area.

Such orthopedic knee bandages are used in particular to support, guide, and stabilize the knee joint, e.g., in activities that create a particular burden on the knee and in sports or in a period of healing after damage to the joint.

Such a knee bandage is usually applied by wrapping the knee bandage over the foot and ankle all the way up to the knee. It is removed in a corresponding manner. One disadvantage of this method of applying and removing a knee bandage is regarded as the fact that the bandage cannot be applied and removed easily over a shoe. In the case of athletic bandages, another factor is that removing the bandage after playing sports is made difficult in particular by an increased adhesion tendency due to perspiration.

Knee bandages are known that permit an adaptation of the knee bandage tension by means of tension elements provided for this purpose and thus also facilitate the application and removal of a knee bandage. Tension belts, adhesive tape, Velcro® strips and the like are generally used, being adjusted to conform to requirements before or after applying the knee bandage.

It is regarded as a disadvantage here that applying tension to and relaxing the knee bandage by means of belts is time-consuming and the uneven tension effect of the belts may cause folds in the knee bandage material which are uncomfortable for the wearer of the knee bandage while also interfering with the effect of the knee bandage.

An object of this invention is to make available a knee bandage which will permit easy removal while nevertheless providing high wearing comfort.

This object is achieved by providing an aid in removing the bandage, said aid are designed as a separation that can be closed by a zipper and extends over some or all of the length of the sheathing body.

When applied in the functional state, the sheathing body has essentially a cylindrical shape or conical shape, whereby the exact design and dimensions being determined by the target group and the intended application of the bandage. The removal aid extends in the longitudinal direction of the sheathing body, preferably extending to the end of the sheathing body at least on one side.

If the separation extends over the complete length of the knee bandage, then in addition to the traditional method of application with the zipper closed, application of the bandage by placing the bandage around the knee while the bandage is open and then closing it with the zipper is also possible. In particular, in the case of such a bandage with a separation running over the entire length of the bandage, this simplifies the removal of the bandage. The bandage as a whole is opened on one side as a result of the opening of the zipper, and then appears to become self-detached from the leg. Therefore, it is no longer necessary to pull the bandage over sweaty skin in the direction of the foot.

In the case of inventive knee bandages with which the separation extends over only a portion of the length of the bandage, a tangential widening of the sheathing body is achieved by opening the zipper. This widening results in only a slight force being required to remove the bandage and additionally, to put on the knee bandage. The zipper permits a rapid and convenient means of establishing the tangential tension on the sheathing body after applying the knee bandage in the widened state, with such a knee bandage with a zipper that does not extend over the entire length, it is advantageous in particular that threading of the zipper pull is omitted because the zipper pull is always connected to both zipper strips. Such threading is difficult in the applied state, in particular, because of the required tangential tension in the sheathing body.

The tangential tension in the sheathing body which occurs in the applied functional state with the zipper closed is mostly homogeneous over the length of the separation. For people of limited mobility in particular, applying and removing such a knee bandage is greatly simplified in comparison with a system using belts, with which several tension elements must be put under tension in succession to create the tangential tension and/or must be opened in succession to release the tangential tension.

In a further embodiment of this invention, a protective structure is provided for the body part, for the separation on an inside of the sheathing body provided for the body part, said protective structure being connected to the sheathing part along at least one side of the separation and forming an intermediate position between the surface of the knee area and the zipper in the applied functional state.

The protective structure is preferably made of a flexible material, in particular a textile material. It fulfills the purpose of separating the skin surface and the zipper from one another. This increases wearing comfort because otherwise irritation or injury to the skin would be possible due to the relative movement between the zipper and the skin surface. In addition, in the case of metallic zippers, this avoids the subjectively unpleasant feeling of cold metal against the skin. Another advantage is that the protective structure prevents skin or hair from being caught in the zipper when opening and closing the zipper after the bandage has been applied.

If the protective structure is connected to only one of the two sides of the separation, it is of such dimensions that it extends tangentially beyond the zipper on the inside after being applied to the knee, so that direct contact between the skin and the zipper is prevented. In the case of such a protective structure connected to only one side of the separation, the material of the protective structure preferably has such a low flexibility that it does not form any folds during or after the process of application and therefore no longer forms a reliable separation between the skin and the zipper. The protective structure is preferably attached to the sheathing body on both sides of the longitudinal edges of the separation. If the protective structure is attached on both sides to the adjacent longitudinal sides of the separation, then it should be of such dimensions and/or designed with respect to the material so that it presents little or no resistance to widening of the sheathing body after opening the zipper. Such a protective structure attached to the sheathing body on both sides of the separation also fulfills the purpose of forming a guidance for the body part when the knee bandage is applied, so that the person wearing the bandage does not inadvertently get a toe, for example, caught in the zipper.

In another embodiment of this invention, the protective structure is made of an elastic material whose modulus of elasticity in the tangential direction is lower than the modulus of elasticity of the sheathing body. This is expedient in particular in the case of a protective structure connected to the sheathing body on both sides of the separation. The elastic material of the protective structure makes it possible on the one hand for the protective structure to allow an ideal widening of the sheathing body for applying and removing the knee bandage in the unstretched state of the sheathing body while on the other hand preventing the protective structure from causing folds or bulges to develop in the stretched state of the knee bandage with the zipper because such folds and bulges are unpleasant against the skin of a person wearing the bandage. The lower modulus of elasticity in comparison with the sheathing body ensures that when the zipper is opened, e.g., for removing and applying the knee bandage, widening of the sheathing body is possible with no problem because the elongation required to accomplish this is permitted by the protective structure without applying any great force. However, no stretching of the sheathing body material itself is necessary for widening.

In another embodiment of this invention, a protective section, in particular a protective cushion, is provided on at least one end area of the zipper, this protective section being arranged between the end area of the zipper and the surface of the knee area when the knee bandage is in the applied functional state.

The protective section preferably consists of a textile material. It shields the skin surface from the end areas of the zipper, which is perceived as unpleasant in contact with skin. The protective section may be attached to the sheathing body on one side of the separation or may also be designed to be in one piece with the sheathing body. Alternatively, the protective section may also be connected to the protective structure.

In another embodiment of this invention, which is based on the preceding, a securing section of the protective section can be folded over onto the outside of the sheathing body of the knee bandage, and fixation means for detachable fixation of the securing section are provided on the outside of the sheathing body. The securing section is preferably made of a textile material. It may be attached in one piece to an interior subsection of the protective section. The fixation means may be designed, for example, as snaps or as a Velcro®-type closure. The securing section achieves the result that there is no contact of the end area of the zipper with the skin due to movement of the knee or an associated slippage of the protective section.

In another embodiment of this invention, the protective section is attached to the protective structure, in particular by sewing, or is designed in one piece with the protective structure.

Such a combination of a protective section and a protective structure can be manufactured easily and inexpensively. Such an embodiment is advantageous in particular, in the case of a protective structure which is attached to the sheathing body on only one side of the separation. The fixation means for attaching the protective section there serve to simultaneously tighten the protective structure and prevent slippage.

In another embodiment of this invention, at least one longitudinal side of the separation has a supporting strand which has a lower flexibility than the material of the sheathing body.

This supporting strand may be formed, for example, by two or more strip sections of the sheathing body material sewn together. Providing such an inventive supporting strand is expedient when applying the knee bandage with the zipper open and also in the functional state. When applying the knee bandage, the supporting strand prevents the material of the sheathing body from folding over and also makes it difficult to close the zipper. In the tightened functional state with the zipper closed, the supporting strand presents an additional stabilization of the knee joint that is to be supported, in particular, in the transverse direction, and thus prevents the joint from assuming a position that would be deleterious from an orthopedic standpoint.

In another embodiment of this invention, the supporting strand includes a supporting strut which is preferably made of plastic and is embedded in at least some sections in the elastic material of the sheathing body.

Such a supporting strut stabilizes the knee especially well and thereby protects the knee joint. The supporting strut may be designed so that it has a greater stiffness across the direction of bending of the knee joint than in the direction of bending.

In another embodiment of this invention, the separation in the applied functional state is arranged on one side of the knee area.

The arrangement of the aid for applying and/or removing the knee bandage on the side of the knee area represents the least possible restriction with respect to wearing comfort for the person wearing the knee bandage. Although the distance between the two ends of the knee bandage changes permanently as a function of the bent position of the knee on both the front side and the back side, the distance between the ends on the sides of the leg is largely constant. The aid for applying and/or removing may be provided on the inside or the outside.

Other objects, advantages and novel features of the present invention will become apparent from the following detailed description of the invention when considered in conjunction with the accompanying drawings.

The reference notation used for the two embodiments is identical for components that are the same or approximately the same.

DETAILED DESCRIPTION

Figure 1:
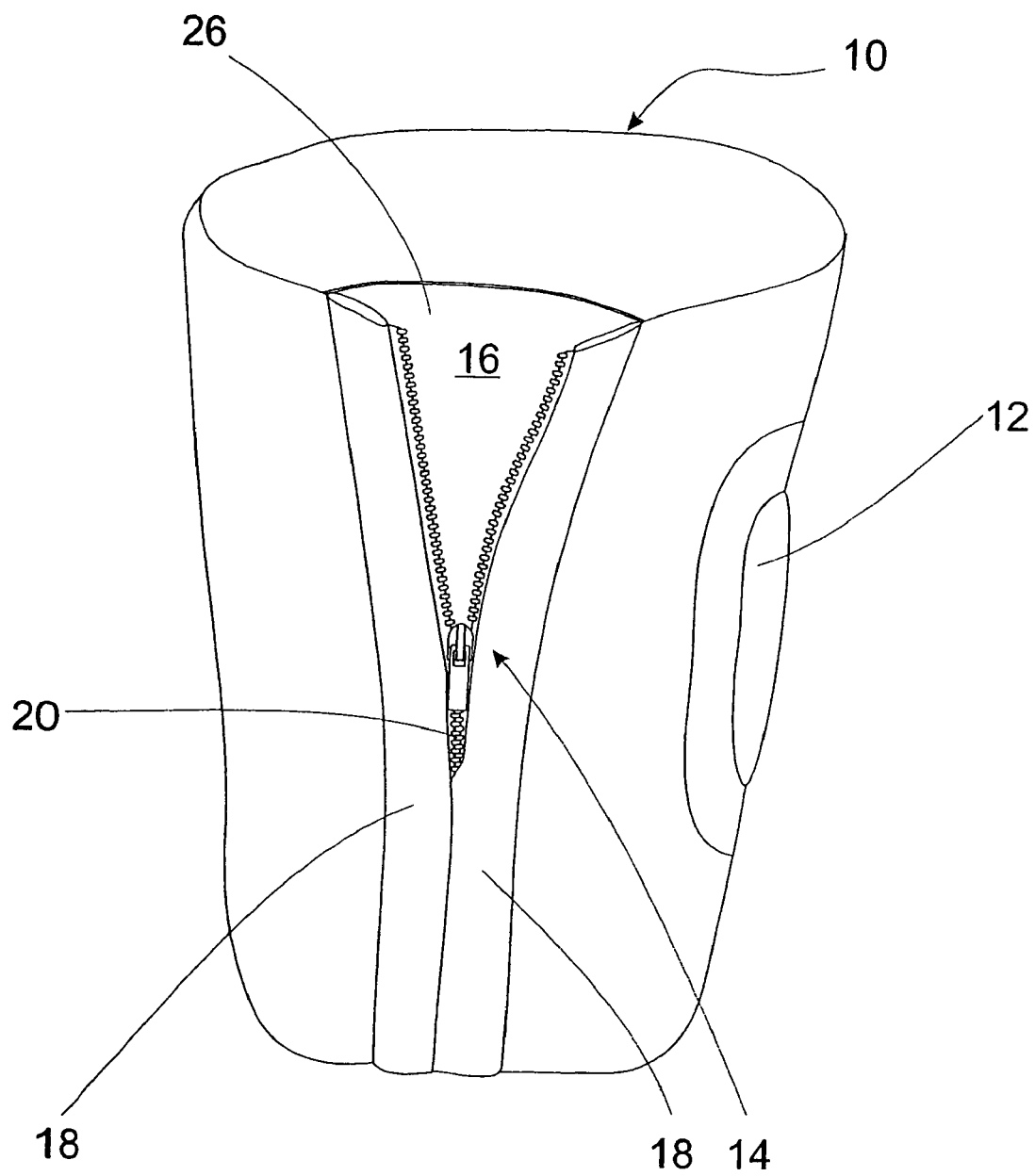
FIG. 1 shows a first embodiment of an inventive knee bandage in a side diagram in the relaxed state with the sheathing body widened and with the zipper open, extending over part of the length of the knee bandage.
Figure 2:
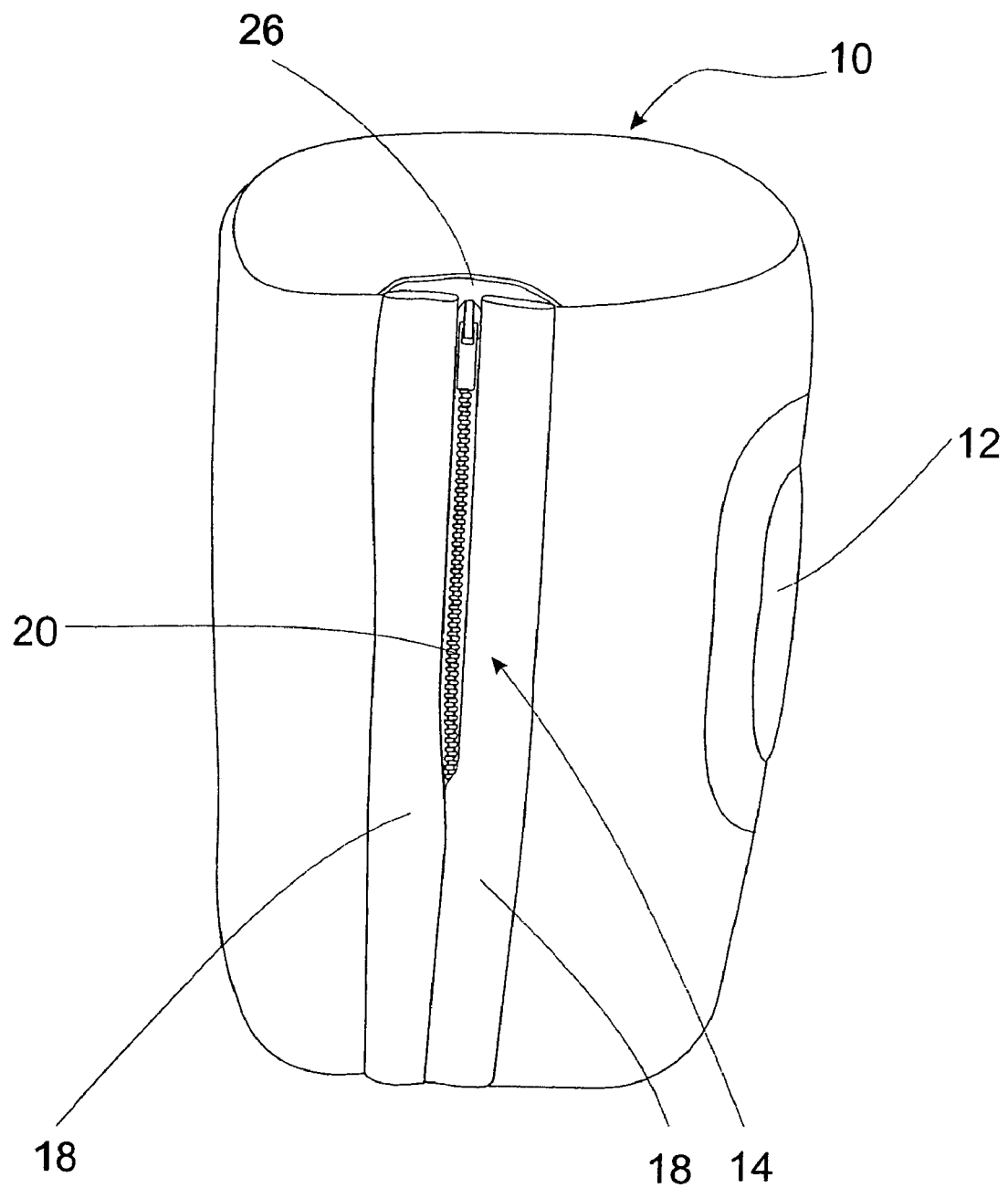
FIG. 2 shows the first embodiment of the knee bandage depicted in FIG. 1 shown here in the tightened state with the zipper closed.

FIG. 1 and FIG. 2 show a first embodiment of the inventive knee bandage. The knee bandage has a cylindrical sheathing body 10 which is equipped with a knee guard 12 on the front side. An aid 14 for applying/removing the bandage is provided on one side of the knee bandage. It extends downwards from the upper end of the sheathing body 10 over approximately two-thirds of the length of the sheathing body 10. This aid 14 in applying/removing the knee bandage has a separation 16. Parallel and adjacent to the separation 16, two supporting edges 18 which extend in the longitudinal direction are provided; their flexibility is lower than the flexibility of the sheathing body 10. The two supporting edges 18 can be connected by a zipper 20 which consists of two side strips and a pull. The side strips are sewn securely onto the supporting edges 18. A textile protective structure 26 which is made of a highly extensible material, is provided on the inside of the aid 14 for applying/removing the knee bandage. The protective structure 26 is sewn to the supporting edges 18 on both sides of the separation 16 and extends in the longitudinal direction of the sheathing body 10 over the entire length of the separation 16.

FIG. 1 shows the relaxed state. In this state the zipper 20 is largely open so that the circumference of the knee bandage on the upper end is enlarged in comparison with a tightened state with the zipper 20 closed. To protect the leg, the protective structure 26 is provided in this relaxed state with the zipper 20 open which is greatly stretched as a result of the widening of the knee bandage. In the state depicted here, it is conveniently possible to apply the knee bandage. Due to the enlarged circumference at the upper end, the leg can be inserted very easily into the knee bandage without a high frictional force between the knee bandage and the body part in the area of the heel or the calf making this process more difficult. The protective structure 26 prevents skin or hair from being caught in the zipper 20 when it is applied. If the knee bandage is situated at the proper level in the desired position, i.e., in the present case in the area of the knee, then the desired tension can be established from an orthopedic standpoint by closing the zipper 20. Even when closing the zipper 20, the protective structure 26 prevents hair or skin from being involved. In this state with the zipper 20 open, removal of the knee bandage is also greatly facilitated because, since the knee bandage is partially relaxed, a lower force is necessary to pull the knee bandage over the calf and the foot.

FIG. 2 shows the knee bandage in the applied functional state. It can be seen here that the zipper 20 is closed, so the knee bandage has a largely cylindrical shape. The protective structure 26 is no longer stretched in this state. The elasticity of the protective structure 26 ensures that the protective structure 26 will not develop any folds in the condition of the knee bandage depicted in FIG. 2 with the zipper 20 closed. Instead, it will lie smoothly on the leg and will thus contribute to a high level of wearing comfort with the knee bandage. Due to the closed zipper 20, a tangential elongation of the knee bandage can occur only by stretching the sheathing body 10. However, since a much greater force is required for this in comparison with the supporting structure 26, the knee bandage ensures the desired permanent supporting and compressing effect on the knee. The supporting edges 18 run largely parallel in the tightened state of the knee bandage and stabilize the knee joint especially in the transverse direction.

Figure 3:
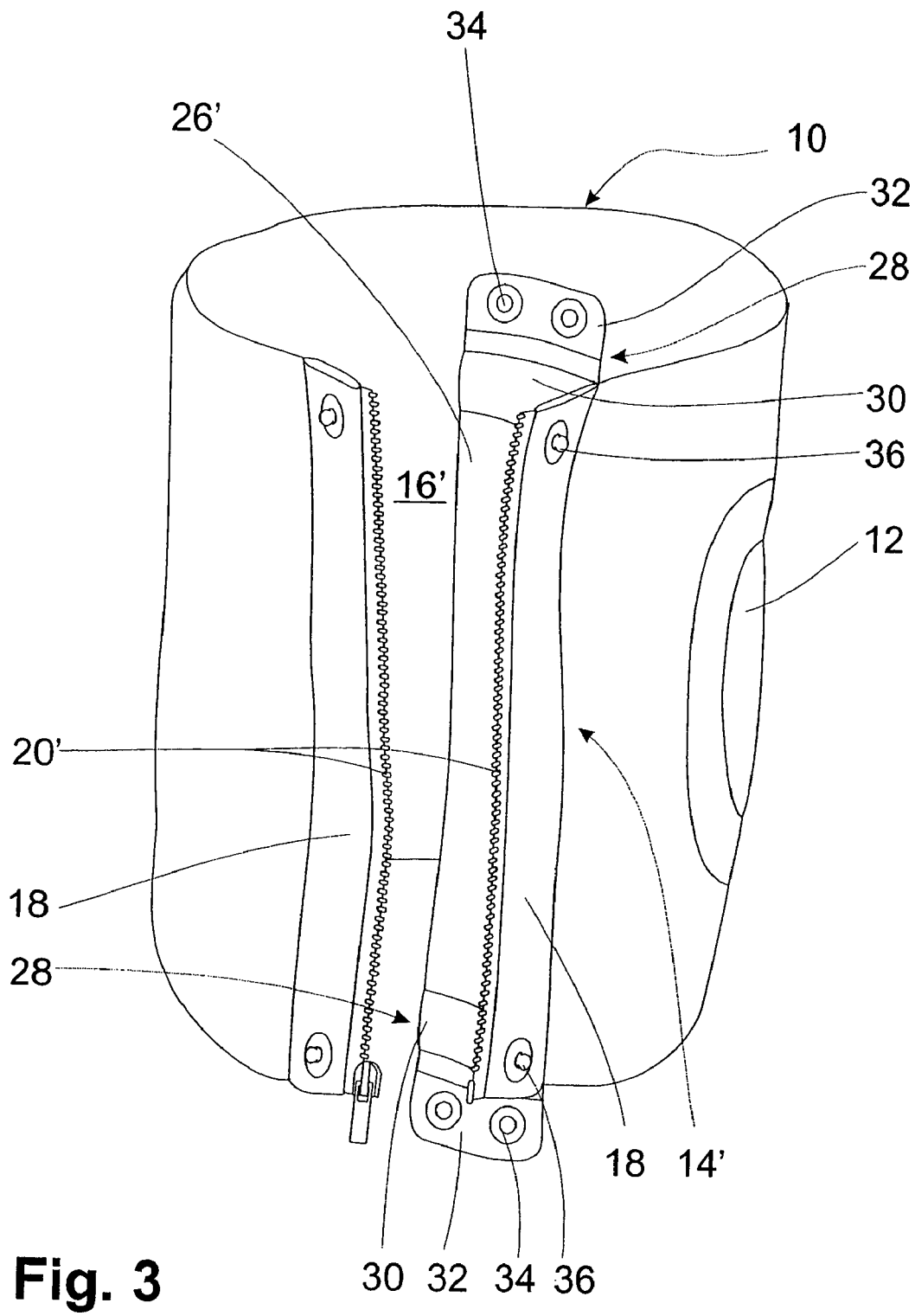
FIG. 3 shows a second embodiment of an inventive knee bandage in a side diagram in the relaxed state with the sheathing body widened and with the zipper open, extending over the total length of the knee bandage.
Figure 4:
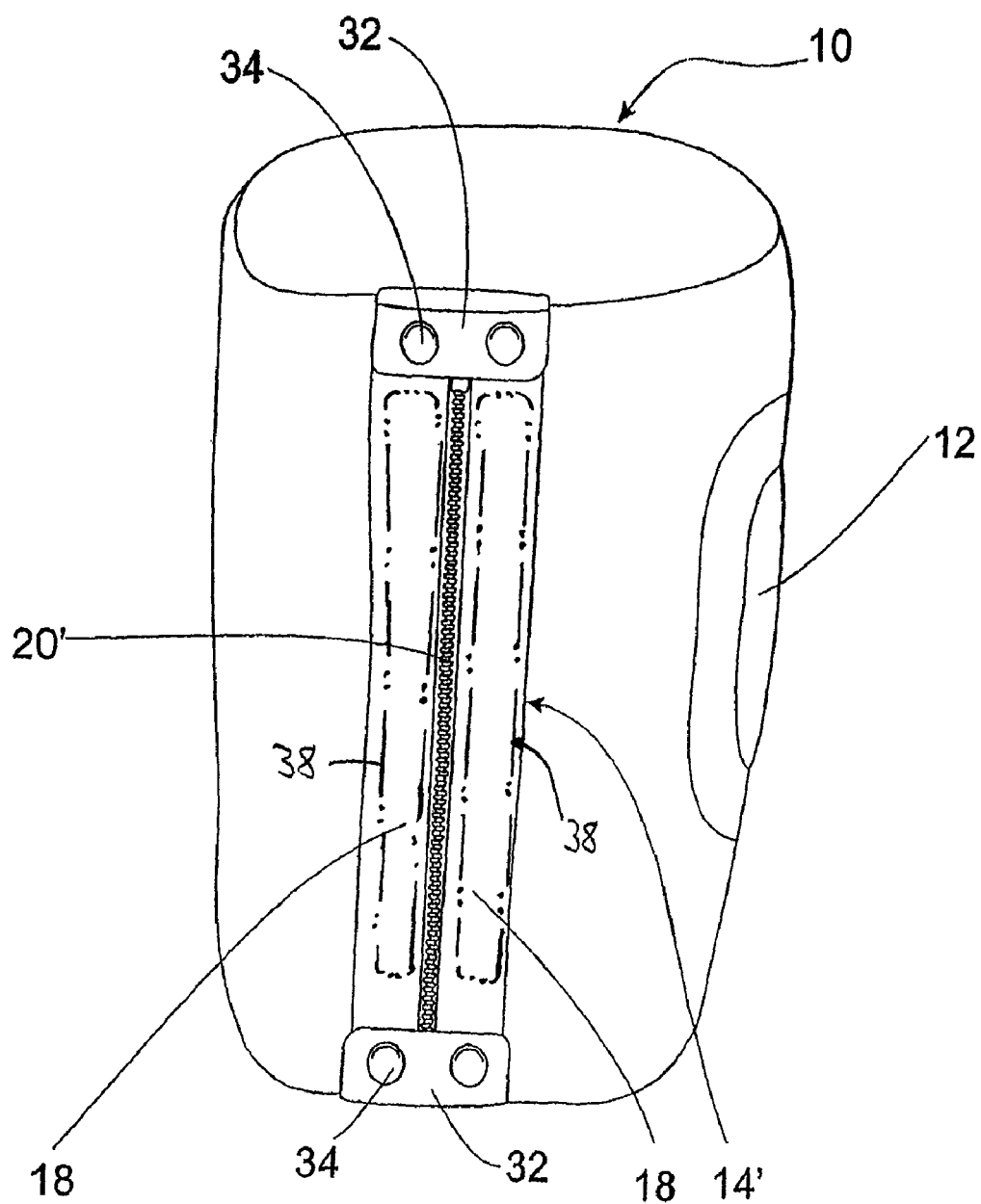
FIG. 4 shows the second embodiment of the knee bandage depicted in FIG. 3 shown here in the tightened state with the zipper closed.

The second embodiment of the knee bandage depicted in FIG. 3 and FIG. 4 differs from the first embodiment in various regards. The aid 14' for applying/removing the knee bandage and having the separation 16' and the zipper 20' extends in this second embodiment over the entire length of the knee bandage. The protective structure 26' is connected to the sheathing body 10 of the knee bandage on only one side and has a lower flexibility than the protective structure 26 of the first embodiment. At the upper and lower ends, the protective structure 26' is connected in one piece to protective cushions 28 which have a subsection 30 that is arranged in such a way that it separates the end areas of the zipper 20' from the skin surface. In addition, the protective cushion 28 has a securing section 32 which in the applied functional state is folded onto the outside of the sheathing body and is secured there with fixation means. In the embodiment depicted here, the fixation means are designed as two snaps each per protective cushion 28, whereby the securing sections 32 of the protective cushions 28 each have two snap-bushing sections 34, while the corresponding snap-connector sections 36 are provided on the supporting edges 18.

FIG. 3 shows the second embodiment of the inventive knee bandage with the zipper 20' open. In this state, the two supporting edges 18 are completely separated from one another so that it is possible to apply the bandage and remove it without having to pull it over the foot and calf. The snaps 34, 36 are open so that the end areas of the zipper 20' are exposed.

FIG. 4 shows the knee bandage in the applied functional state. The zipper 20' is completely closed. The securing sections 32 of the protective cushion 28 are folded over the ends of the sheathing body 10 on the upper and lower ends of the knee bandage and secured on the outside of the bandage by means of the snaps 34, 36 in that the snap bushing sections 34 are locked on the snap-plug sections 36. This ensures that the protective sections 30 of the protective cushion 28 will not slip even with a marked movement of the knee and with thus allow direct contact of the end areas of the zipper 20' with the skin. Also shown in FIG. 4 in phantom view are the previously-mentioned supporting struts 38, which may be sewn into supporting edges 18 to help stabilize the knee.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Medical knee bandage having a knee guard affixed to a sheathing body made of material that is elastic in at least some sections and is open on opposite ends, and in an applied functional state, said state being when the sheathing body is located about a human knee, the sheathing body forms a closed sheathing material that is under stress elastically and tangentially in a region around the human knee, wherein an aid is provided for removing the bandage, this aid being designed as a separation having a zipper and a protective structure located between the zipper and an inside region of the sheathing body, the aid extending over at least a portion of the length of the sheathing body in an area of the sheathing body which is opposite one of a lateral and a medial side of the human knee when the sheathing body is in the applied functional state, and further wherein at least one longitudinal side of the separation has a supporting strand which has a lower flexibility than the material of the sheathing body.

2. Knee bandage as claimed in claim 1, wherein the protective structure provided for the separation on an inside of the sheathing body is attached to the sheathing body along at least one side of the separation and in the applied functional state it forms an intermediate layer between a surface of the knee area and the zipper.

3. Knee bandage as claimed in claim 2, wherein the protective structure is made of an elastic material whose modulus of elasticity in the tangential direction is lower than the modulus of elasticity of the sheathing body.

4. Knee bandage as claimed in claim 1, wherein the protective section is provided on at least one end area of the zipper and in the applied functional state of the knee bandage, this protective section is arranged between the end area of the zipper and the surface of the knee area.

5. Knee bandage as claimed in claim 4, wherein a securing section of the protective section can be folded over onto the outside of the sheathing body of the knee bandage and that fixation means for detachable fixation of the securing section are provided on the outside of the sheathing body.

6. Knee bandage as claimed in claim 4, wherein the protective structure provided for the separation on an inside of the sheathing body protective section is connected to a protective structure provided for the separation on an inside of the sheathing body by sewing or is formed in one piece with the protective structure.

7. Knee bandage as claimed in claim 1, wherein the supporting strand comprises a supporting strut made of plastic and embedded in at least some sections in the elastic material of the sheathing body.

8. Knee bandage as claimed in claim 1, wherein the separation is arranged on one side of the knee area in the applied functional state.

* * * * *